(12) United States Patent
Lee et al.

(10) Patent No.: US 9,983,071 B2
(45) Date of Patent: May 29, 2018

(54) TENDON ACTUATOR UNIT

(71) Applicant: Oceaneering International, Inc., Houston, TX (US)

(72) Inventors: Jason Lee, Houston, TX (US); Austin Lovan, Webster, TX (US); Roger Rovekamp, League City, TX (US)

(73) Assignee: OCEANEERING INTERNATIONAL, INC., Houston, TX (US)

( * ) Notice: Subject to any disclaimer, the term of this patent is extended or adjusted under 35 U.S.C. 154(b) by 0 days. days.

(21) Appl. No.: 15/178,630

(22) Filed: Jun. 10, 2016

(65) Prior Publication Data

US 2016/0363517 A1 Dec. 15, 2016

Related U.S. Application Data

(60) Provisional application No. 62/173,589, filed on Jun. 10, 2015.

(51) Int. Cl.
G01N 3/08 (2006.01)
G01L 1/00 (2006.01)
F16H 55/00 (2006.01)
A61B 34/30 (2016.01)

(52) U.S. Cl.
CPC ............ G01L 1/00 (2013.01); F16H 55/00 (2013.01); *A61B 34/30* (2016.02); *G01N 3/08* (2013.01)

(58) Field of Classification Search
CPC .......... A61B 34/30; G01L 1/00; F16H 55/00; G01N 3/08

USPC .............................. 73/826, 862.392-862.393
See application file for complete search history.

(56) References Cited

U.S. PATENT DOCUMENTS

| | | | | |
|---|---|---|---|---|
| 4,804,220 A * | 2/1989 | Rosheim | .................. | B25J 9/104 294/111 |
| 5,502,363 A * | 3/1996 | Tasch | ......................... | B25J 9/12 318/568.1 |
| 6,042,555 A * | 3/2000 | Kramer | .................. | A61B 5/225 600/595 |
| 8,551,079 B2 * | 10/2013 | Anderson | .............. | A61B 34/71 128/898 |
| 2010/0077810 A1 * | 4/2010 | De Franceschi | ....... | G01G 15/00 70/283.1 |
| 2011/0056321 A1 * | 3/2011 | Sim | ........................ | B25J 9/1025 74/490.04 |
| 2012/0283845 A1 * | 11/2012 | Herr | ......................... | A61F 2/66 623/24 |
| 2014/0228880 A1 * | 8/2014 | Bisson | ............... | A61B 17/0401 606/232 |
| 2015/0352725 A1 * | 12/2015 | Santos | .................. | B25J 9/1045 74/490.05 |

* cited by examiner

Primary Examiner — Max Noori
(74) Attorney, Agent, or Firm — Maze IP Law, PC

(57) ABSTRACT

A tendon actuator unit comprises a housing; a pulley disposed within the housing, the pulley comprising a screw-like groove about a predetermined portion of an outer surface of the pulley configured to accept a predetermined length of a cable; a motor disposed in or proximate to the housing and operatively in communication with the pulley; one or more online cable sensors; one or more sensor rollers; and one or more conduit force sensors.

15 Claims, 5 Drawing Sheets

TENDON ACTUATOR UNIT

RELATION TO PRIOR APPLICATIONS

This application claims priority through U.S. Provisional Application No. 62/173,589, filed on Jun. 10, 2015.

FIELD OF THE INVENTION

The invention relates generally to tendon actuation units.

FIGURES

Various figures are included herein which illustrate aspects of embodiments of the disclosed invention.

DESCRIPTION OF VARIOUS EMBODIMENTS

Figure 1:
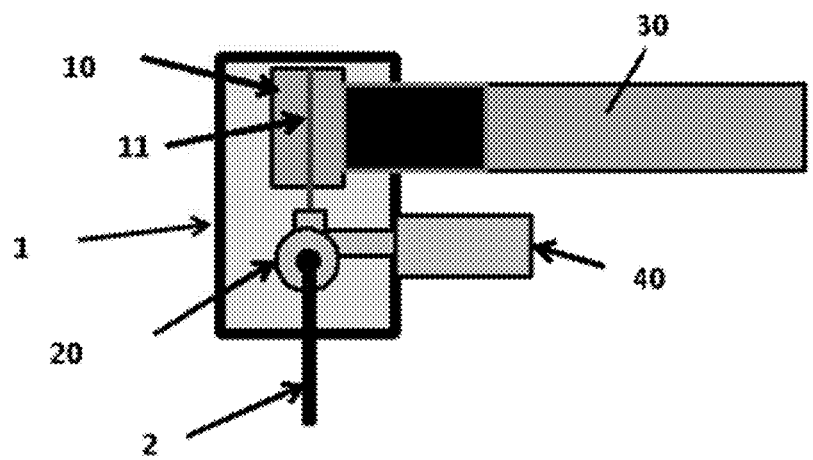
FIG. 1 is a schematic cut-away view of an exemplary tendon actuation unit.

Referring generally to FIG. 1, cable 11, referred to herein sometimes as a tendon, is operatively attached to pulley 10 for controlled deployment. Forces on cable 11 may be monitored using one or more force sensor, which can include on-line tension sensors that measure tendon force directly and/or conduit force sensors that infer tendon force through conduit compression forces. On-line tension sensors may indirectly measure tendon force by measuring a radial force created by the tendon as it passes over a roller located on a bearing journal of a sensor. The on-line tension sensors can be used for control or simply as a redundant force sensor.

Moreover, conduit force sensors may be present and used to measure compression force from a conduit as cable 11 attempts to straighten itself. This compression force can be used to infer tendon force and thus provide an indirect measurement of tendon force. The conduit force sensors can be used for control or simply as a redundant force sensor.

In each embodiment described herein, motor design may accommodate a tendon Brummel which may be loop hooked or otherwise attached onto one or more pulleys and comprises tangential exit points. Typically, the pulley diameter is based on motor selection, e.g. speed and torque requirements, and the pulley length is based on maximum tendon travel. In an embodiment, pulley length is designed for 12 inches of linear travel, which is around 3-4 inches more than required, and comprises around 7 wraps required for desired range.

Figure 2:
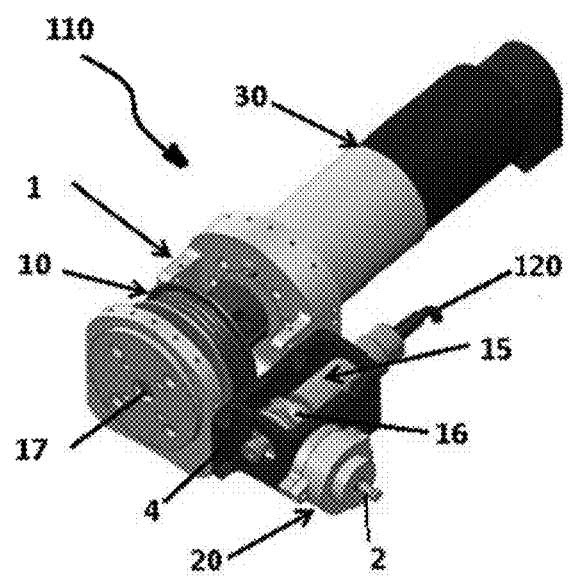
FIG. 2 is a cut-away view in partial perspective of an tendon actuation unit.

In a first embodiment illustrated in FIG. 2, tendon actuator unit 110 comprises housing 1; pulley 10 disposed within housing 1, where pulley 10 comprises a screw-like groove about a predetermined portion of an outer surface of pulley 10 and where pulley 10 is configured to accept a predetermined length of cable 11 (FIG. 1) about the outer surface at least partially within the screw-like groove; motor 30 disposed proximate housing 1 and operatively in communication with pulley 10; a radial bearing 17; sensor bracket 4 connected to housing 1; one or more online cable sensors 15 disposed at least partially within sensor bracket 4, where online cable sensor 15 comprises one or more sensor outputs 120; sensor roller 16 operatively in communication with online cable sensor 15 and configured to be operatively in communication with cable 11 when cable 11 is present; and one or more conduit force sensors 20 connected to sensor bracket 4 and configured to be operatively in communication with cable 11 when cable 11 is present, at least one conduit force sensor 20 comprising cable conduit 2 adapted to accept cable 11 therethrough.

Typically, the dimensions, e.g. depth and/or width and/or wall thickness, of the screw-like groove of pulley 10 are configured to prevent cable 11 from traveling in adjacent grooves.

Cable 11 is typically terminated at pulley 10 in any appropriate manner, e.g. removably or fixedly attached to pulley 10.

Cable conduit 2 is typically grounded to housing 1.

In certain embodiments, cable sensors 15 comprise one or more modular sensors.

Figure 3:
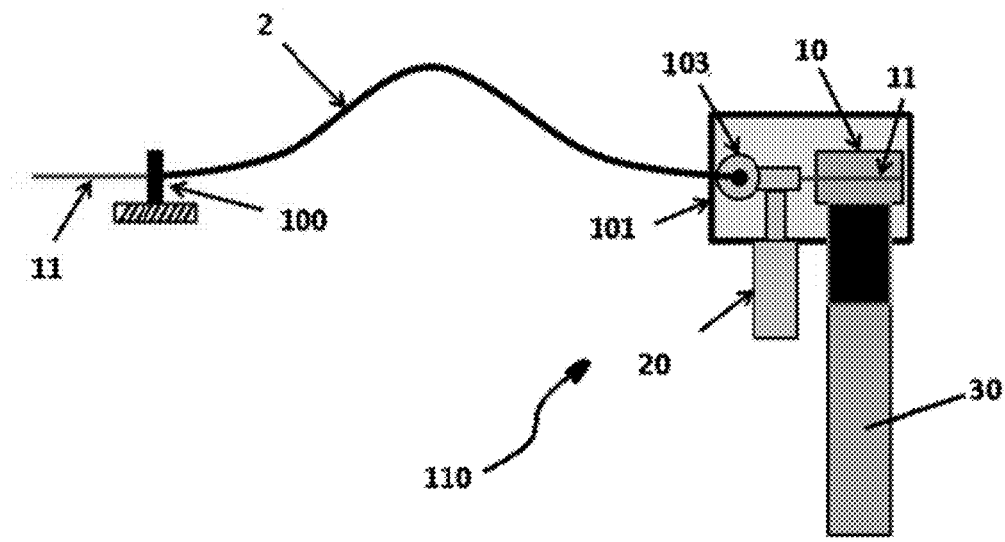
FIG. 3 is a schematic cut-away view of an exemplary tendon actuation unit showing additional sensors.
Figure 9:
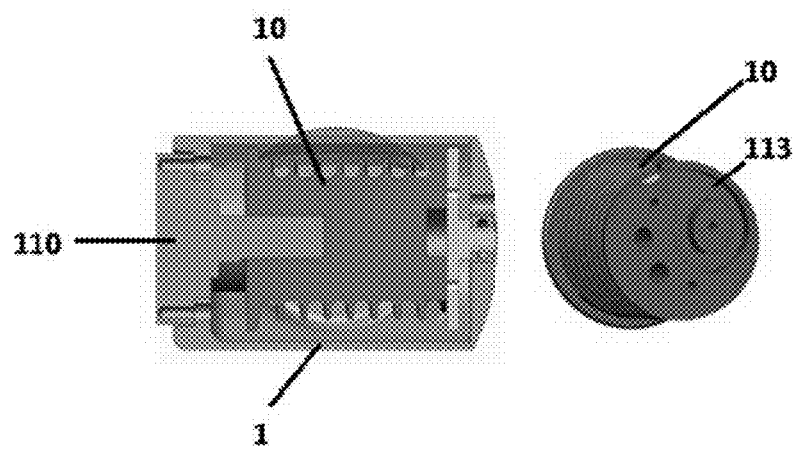
FIG. 9 is a cut-away view in partial perspective of an exemplary tendon actuation unit pulley.

Referring additionally to FIG. 3, one or more distal sensors 100 may be present and operatively connected to cable conduit 2. In addition, one or more proximal conduit force sensors 103 may be present, typically grounded at proximal conduit ground 101, and cable 11 may be routed through proximal conduit 2 to a point away from tendon actuator unit 110 (FIG. 9).

Figure 5:
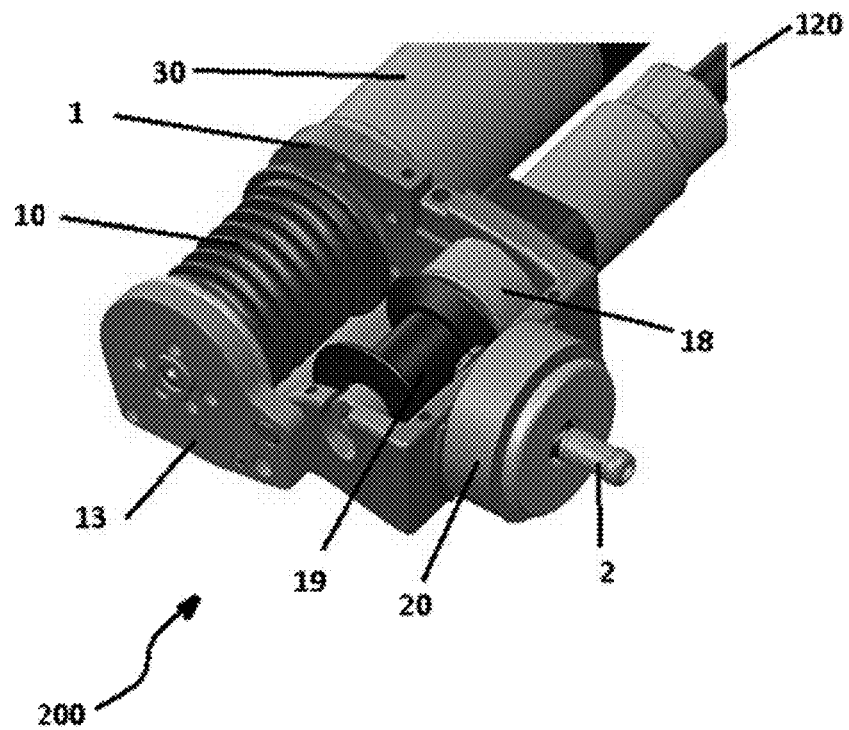
FIG. 5 is a cut-away view in partial perspective of an exemplary tendon actuation unit.
Figure 7:
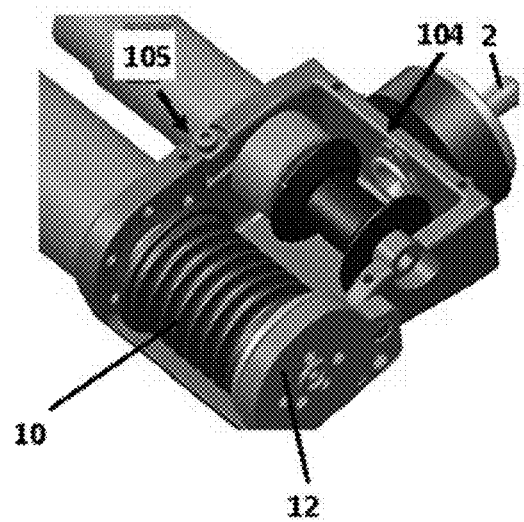
FIG. 7 is a cut-away view in partial perspective of an exemplary tendon actuation unit.
Figure 8:
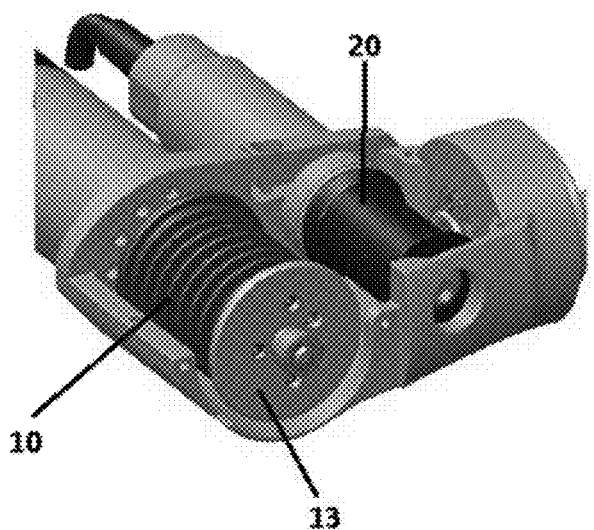
FIG. 8 is a cut-away view in partial perspective of an exemplary tendon actuation unit.

Referring now to FIG. 5, in a further embodiment integrated tendon actuator unit 200 comprises housing 1; pulley 10 disposed fully within housing 1, where pulley 10 comprises a screw-like groove about a predetermined portion of an outer surface of pulley 10 and where pulley 10 is configured to accept a predetermined length of cable 11 (FIG. 1) about the outer surface at least partially within the screw-like groove; pulley retainer 12 (FIG. 7) in communication with the pulley 10, where pulley retainer 12 is connected to housing 1; one or more pulley washers 13 disposed intermediate pulley 10 and pulley retainer 12; one or more online cable sensors 18 disposed within housing 1 where online cable sensors 18 are adapted to indirectly measure tendon force radial to pulley 10, where online cable sensors 18 comprise one or more sensor outputs 120; sensor roller 19 disposed at least partially within housing 1, where sensor roller 19 is operatively in communication with at least one online cable sensor 18 and configured to be operatively in communication with cable 11 when cable 11 is present; one or more conduit force sensors 20 connected to housing 1 and configured to be operatively in communication with cable 11 when cable 11 is present, at least one conduit force sensor 20 comprising cable conduit 2 adapted to accept cable 11 therethrough and adapted to measure compression force from cable conduit 2 (FIG. 3) as cable 11 attempts to straighten itself; and motor 30 disposed proximate to housing 1 and operatively in communication with pulley 10.

In a preferred embodiment, housing 1 comprises a unified bracket design which provides a reduced number of parts and fasteners. In this embodiment, bracket fasteners cannot back out for safety.

Conduit force sensor 20 may comprise an integrated sensor. In certain embodiments, one or more retaining rings 104 (FIG. 7) may be present and adapted to secure conduit force sensor 20 to the housing 1. In these embodiments, conduit force sensor 20 is clamped instead of using locknuts and there are a reduced number of fasteners which also comprise reduced size.

Conduit force sensors 20 are typically located proximally to and/or integrated into housing 1, although they can also be located along the length of conduit 2 (FIG. 3) or at a distal conduit grounding point proximate a proximal end of conduit 2.

One or more distal sensors 100 (FIG. 3) may be present and operatively in communication with cable 11, each such distal sensor 100 being disposed at a predetermined location away from housing 1.

Further, one or more proximal sensors 103 (FIG. 3) may be present and connected to one or more associated cable conduits 2 (FIG. 3).

Figure 10:
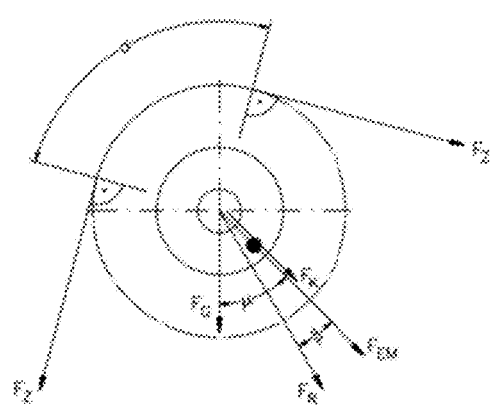
FIG. 10 is a vector diagram illustrating sensor position based on sensor load capability and a tangential angle of a cable against a roller.

One or more sensor clamps 105 (FIG. 7) may be present and adapted to secure online cable sensor 18 to housing 1. Further, online cable sensor 18 may be positioned within housing 1 at a predetermined position based on sensor load capabilities and the tangential angle of cable 11 with respect to pulley 10. This predetermined position may be determined using the formula, as illustrated in FIG. 10:

$$F_R = 2 \cdot F_Z \cdot \sin\frac{\alpha}{2}$$

In certain embodiments, online cable sensor 18 is cantilevered from pulley 10 to account for the entire pulley length and changes in tendon angle.

Typically, sensor roller 19 is configured to allow cable 11 (FIG. 3) to slide along sensor roller 19, e.g. axially, as it travels from the first groove to the last groove on pulley 10. Typically, cable 11 is configured to travel from a first pulley groove to a last pulley groove.

Figure 6:
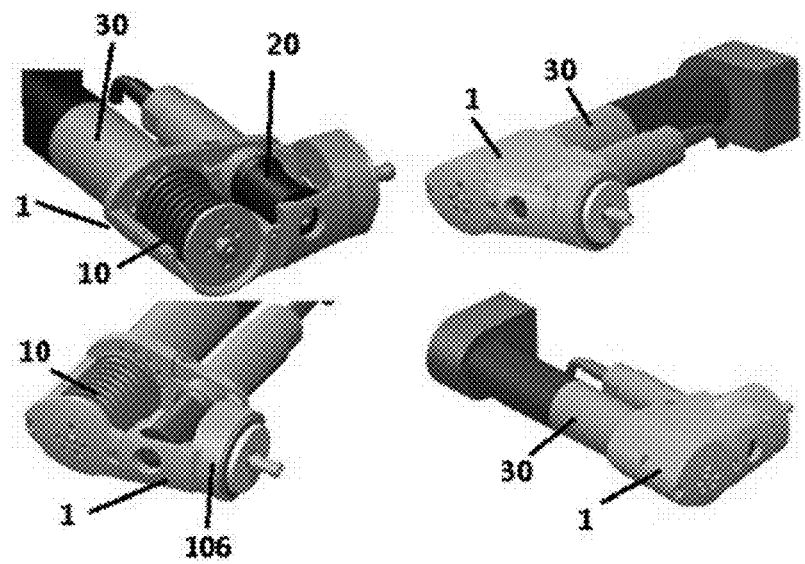
FIG. 6 are four views, two in cut-away, in partial perspective of an exemplary tendon actuation unit.

Housing 1 may further comprise one or more sensor ports 106 (FIG. 6) configured to accept conduit force sensor 20 therein, typically one conduit force sensor 20 per sensor port 6.

Pulley retainer 12 (FIG. 7) may be removably connected to housing 1.

Figure 4:
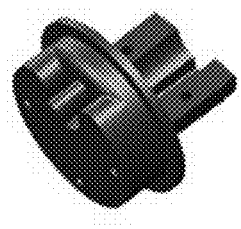
FIG. 4 is a view in partial perspective of an exemplary tendon actuation unit pulley.

As illustrated in FIG. 4 and FIG. 9, cable 11 may be attached to pulley at hook 113 which may be cantilevered.

The foregoing disclosure and description of the inventions are illustrative and explanatory. Various changes in the size, shape, and materials, as well as in the details of the illustrative construction and/or an illustrative method may be made without departing from the spirit of the invention.

What is claimed is:

1. A tendon actuator unit, comprising:
   a. a housing;
   b. a pulley disposed within the housing, the pulley comprising a screw-like groove about a predetermined portion of an outer surface of the pulley, the pulley configured to accept a predetermined length of a cable about its outer surface at least partially within the screw-like groove;
   c. a motor disposed proximate the housing and operatively in communication with the pulley;
   d. a radial bearing;
   e. a sensor bracket connected to the housing;
   f. an online cable sensor disposed within the sensor bracket, the online cable sensor comprising a sensor output;
   g. a sensor roller operatively in communication with the online cable sensor and configured to be operatively in communication with the cable when the cable is present; and
   h. a conduit force sensor connected to sensor bracket and configured to be operatively in communication with the cable when the cable is present, the conduit force sensor comprising a cable conduit adapted to accept the cable therethrough.

2. The tendon actuator unit of claim 1, wherein the online cable sensor comprises a modular sensor.

3. The tendon actuator unit of claim 1, further comprising a distal cable sensor connected to the conduit.

4. An integrated tendon actuator unit, comprising:
   a. a housing;
   b. a pulley disposed fully within the housing, the pulley comprising a screw-like groove about a predetermined portion of an outer surface of the pulley, the pulley configured to accept a predetermined length of a cable about its outer surface at least partially within the screw-like groove;
   c. a pulley retainer in communication with the pulley, the pulley retainer connected to the housing;
   d. a pulley washer disposed intermediate the pulley and the pulley retainer;
   e. an online cable sensor disposed within the housing, the online cable sensor adapted to indirectly measure tendon force, the online cable sensor comprising a sensor output;
   f. a sensor roller disposed within the housing, the sensor roller operatively in communication with the online cable sensor and configured to be operatively in communication with the cable when the cable is present;
   g. a conduit force sensor connected to the housing and configured to be operatively in communication with the cable when the cable is present, the conduit force sensor comprising a cable conduit adapted to accept the cable therethrough, the conduit force sensor adapted to measure compression force from conduit as the cable attempts to straighten itself; and
   h. a motor disposed proximate to the housing, the motor operatively in communication with the pulley.

5. The tendon actuator unit of claim 4, wherein the sensor comprises an integrated sensor.

6. The tendon actuator unit of claim 4, further comprising a distal sensor operatively in communication with the cable, the distal sensor disposed at a predetermined location away from the housing.

7. The tendon actuator unit of claim 4, further comprising a proximal cable sensor connected to the conduit.

8. The tendon actuator unit of claim 4, further comprising a retaining ring in communication with the conduit force sensor to secure the conduit force sensor to the housing.

9. The tendon actuator unit of claim 4, further comprising a sensor clamp adapted to secure the online cable sensor to the housing.

10. The tendon actuator unit of claim 4, wherein the online cable sensor is positioned within the housing at a predetermined position based on sensor load capabilities and the cable's tangential angle with respect to the pulley.

11. The tendon actuator unit of claim 4, wherein the online cable sensor is cantilevered from the pulley to account for the entire pulley length and changes in tendon angle.

12. The tendon actuator unit of claim 4, wherein the sensor roller is configured to allow the cable to slide along the sensor roller.

13. The tendon actuator unit of claim 12, wherein the cable is configured to travel from a first pulley groove to a last pulley groove.

14. The tendon actuator unit of claim 4, wherein the housing comprises a sensor port configured to accept the conduit force sensor therein.

15. The tendon actuator unit of claim 4, wherein the pulley retainer is removably connected to the housing.

* * * * *